(12) United States Patent
Cotton

(10) Patent No.: US 9,393,158 B2
(45) Date of Patent: Jul. 19, 2016

(54) NON-ADHERENT WOUND DRESSING

(75) Inventor: Stephen Cotton, Nottingham (GB)

(73) Assignee: Brightwake Limited, Kirby-in-Ashfield, Nottinghamshire (GB)

(*) Notice: Subject to any disclaimer, the term of this patent is extended or adjusted under 35 U.S.C. 154(b) by 0 days.

(21) Appl. No.: 13/594,552

(22) Filed: Aug. 24, 2012

(65) Prior Publication Data

US 2013/0053748 A1 Feb. 28, 2013

(30) Foreign Application Priority Data

Aug. 25, 2011 (GB) .................. 1114718.8

(51) Int. Cl.
| | | |
|---|---|---|
| A61F 13/00 | (2006.01) | |
| D06N 3/00 | (2006.01) | |
| A61L 15/26 | (2006.01) | |
| A61L 15/42 | (2006.01) | |
| D06M 15/643 | (2006.01) | |
| D06N 3/12 | (2006.01) | |
| D06M 101/38 | (2006.01) | |

(52) U.S. Cl.
CPC ..... *A61F 13/00017* (2013.01); *A61F 13/00004* (2013.01); *A61F 13/00008* (2013.01); *A61F 13/00029* (2013.01); *A61F 13/00034* (2013.01); *A61F 13/00038* (2013.01); *A61F 13/00987* (2013.01); *A61F 13/00991* (2013.01); *A61L 15/26* (2013.01); *A61L 15/42* (2013.01); *D06M 15/643* (2013.01); *D06N 3/0011* (2013.01); *D06N 3/128* (2013.01); *A61F 13/00* (2013.01); *A61F 2013/00217* (2013.01); *A61L 2420/08* (2013.01); *D06M 2101/38* (2013.01); *D06N 2201/0281* (2013.01); *D06N 2211/18* (2013.01); *D06N 2213/04* (2013.01)

(58) Field of Classification Search
CPC .............. A61F 13/00; A61F 13/00004; A61F 13/00008; A61F 13/00017; A61F 13/00021; A61F 13/00029; A61F 13/00987; A61F 13/00991; A61F 13/00995; A61F 2013/00; A61F 2013/00089; A61F 2013/00217; A61F 13/00034; A61F 13/00038
USPC .................. 602/41–43, 45, 47, 900
See application file for complete search history.

(56) References Cited

U.S. PATENT DOCUMENTS

| | | |
|---|---|---|
| 2,720,477 A | 10/1955 | Lancaster |
| 2,750,942 A | 6/1956 | Robson |
| 3,042,549 A | 7/1962 | Arnold et al. |
| 3,645,264 A | 2/1972 | Gallagher |
| 4,034,751 A | 7/1977 | Hung |

(Continued)

FOREIGN PATENT DOCUMENTS

| | | |
|---|---|---|
| BE | 821734 A1 | 2/1975 |
| CA | 1306701 C | 8/1992 |

(Continued)

OTHER PUBLICATIONS

Kirk Cantor, Blown Film Extrusion: An Introduction, Hanser Gardner Publications, Inc., Cincinnati, Ohio (2006).

(Continued)

*Primary Examiner* — Keri J Nelson
(74) *Attorney, Agent, or Firm* — LeClairRyan, a Professional Corporation

(57) ABSTRACT

A non-adherent wound dressing (1) comprises a substrate (2) in the form of a perforated sheet of melt-blown non-woven material. The substrate (2) is impregnated with, and coated on both sides with, a silicone gel (3).

16 Claims, 3 Drawing Sheets

(56) References Cited

U.S. PATENT DOCUMENTS

| | | |
|---|---|---|
| 4,226,232 A | 10/1980 | Spence |
| 4,286,592 A | 9/1981 | Chandrasekaran |
| 4,346,700 A | 8/1982 | Dunshee |
| 4,353,945 A | 10/1982 | Sampson |
| 4,423,101 A | 12/1983 | Willstead |
| 4,427,425 A | 1/1984 | Briggs et al. |
| 4,550,725 A | 11/1985 | Wishman |
| 4,598,004 A | 7/1986 | Heinecke |
| 4,616,644 A | 10/1986 | Saferstein et al. |
| 4,621,029 A | 11/1986 | Kawaguchi |
| 4,630,603 A | 12/1986 | Greenway |
| 4,655,767 A | 4/1987 | Woodard et al. |
| 4,660,553 A | 4/1987 | Naylor et al. |
| 4,664,662 A | 5/1987 | Webster |
| 4,696,854 A | 9/1987 | Ethier |
| 4,787,380 A | 11/1988 | Scott |
| 4,815,457 A | 3/1989 | Mazars et al. |
| 4,838,253 A | 6/1989 | Brassington et al. |
| 4,867,150 A | 9/1989 | Gilbert |
| 4,921,704 A | 5/1990 | Fabo |
| 4,947,877 A | 8/1990 | Meyer et al. |
| 4,997,425 A | 3/1991 | Shioya et al. |
| 5,004,465 A | 4/1991 | Ternström et al. |
| 5,042,466 A | 8/1991 | McKnight |
| 5,052,381 A | 10/1991 | Gilbert et al. |
| 5,088,483 A | 2/1992 | Heinecke |
| 5,123,900 A | 6/1992 | Wick |
| 5,153,040 A | 10/1992 | Faasse, Jr. |
| 5,158,555 A | 10/1992 | Porzilli |
| 5,160,328 A | 11/1992 | Cartmell et al. |
| 5,167,613 A | 12/1992 | Karami et al. |
| 5,176,663 A | 1/1993 | Svedman et al. |
| 5,230,701 A | 7/1993 | Meyer et al. |
| 5,322,729 A | 6/1994 | Heeter et al. |
| 5,340,363 A | 8/1994 | Fabo |
| 5,409,472 A | 4/1995 | Rawlings et al. |
| 5,415,865 A | 5/1995 | Söderberg et al. |
| 5,512,041 A | 4/1996 | Bogart |
| 5,524,765 A | 6/1996 | Gutentag |
| 5,540,922 A | 7/1996 | Fabo |
| 5,556,375 A | 9/1996 | Ewall |
| 5,635,201 A | 6/1997 | Fabo |
| 5,650,450 A | 7/1997 | Lovette et al. |
| 5,728,085 A | 3/1998 | Widlund et al. |
| 5,861,348 A | 1/1999 | Kase |
| 5,902,260 A | 5/1999 | Gilman et al. |
| 5,939,339 A | 8/1999 | Delmore et al. |
| 6,040,492 A | 3/2000 | Lindquist et al. |
| 6,051,747 A | 4/2000 | Lindqvist et al. |
| 6,231,872 B1 | 5/2001 | Mooney et al. |
| 6,280,840 B1 | 8/2001 | Lühmann et al. |
| 6,479,724 B1 | 11/2002 | Areskoug et al. |
| 6,486,378 B1 | 11/2002 | Areskoug et al. |
| 6,541,089 B1 | 4/2003 | Hamerski et al. |
| 6,566,575 B1 | 5/2003 | Stickels et al. |
| 6,787,682 B2 | 9/2004 | Gilman |
| 6,846,508 B1 | 1/2005 | Colas et al. |
| 7,066,182 B1* | 6/2006 | Dunshee ............... 128/888 |
| 7,161,056 B2 | 1/2007 | Gudnason et al. |
| 7,309,809 B2* | 12/2007 | Smith et al. ........... 602/57 |
| 2002/0106471 A1 | 8/2002 | Kuo et al. |
| 2002/0193723 A1 | 12/2002 | Batdorf, Sr. et al. |
| 2003/0026967 A1 | 2/2003 | Joseph et al. |
| 2003/0220596 A1 | 11/2003 | Dunshee |
| 2003/0229326 A1 | 12/2003 | Hovis et al. |
| 2004/0092855 A1 | 5/2004 | Fabo |
| 2004/0096489 A1 | 5/2004 | Fabo |
| 2004/0127835 A1 | 7/2004 | Sigurjonsson et al. |
| 2004/0143220 A1 | 7/2004 | Worthley |
| 2004/0181198 A1 | 9/2004 | Farbrot et al. |
| 2004/0249328 A1 | 12/2004 | Linnane et al. |
| 2005/0059918 A1 | 3/2005 | Sigurjonsson et al. |
| 2005/0215932 A1 | 9/2005 | Sigurjonsson et al. |
| 2005/0233072 A1 | 10/2005 | Stephan et al. |
| 2005/0276965 A1 | 12/2005 | Etchells |
| 2006/0228318 A1 | 10/2006 | Fabo |
| 2008/0113572 A1* | 5/2008 | Ragaru et al. ............ 442/1 |
| 2010/0159192 A1 | 6/2010 | Cotton |
| 2010/0267302 A1* | 10/2010 | Kantner et al. ........ 442/71 |
| 2011/0070391 A1 | 3/2011 | Cotton |
| 2011/0160686 A1 | 6/2011 | Ueda et al. |

FOREIGN PATENT DOCUMENTS

| | | |
|---|---|---|
| CN | 1775301 A1 | 5/2005 |
| DE | 2007499 A1 | 9/1971 |
| DE | 3032092 A1 | 4/1982 |
| DE | 3204582 A1 | 8/1983 |
| DE | 3726736 A1 | 2/1988 |
| EP | 0092999 A2 | 11/1983 |
| EP | 0 100 148 A1 | 2/1984 |
| EP | 0 117 632 A2 | 9/1984 |
| EP | 0 169 184 A1 | 1/1986 |
| EP | 0 210 968 A2 | 2/1987 |
| EP | 0 250 125 A2 | 12/1987 |
| EP | 0 251 810 A2 | 1/1988 |
| EP | 0 261 167 A1 | 3/1988 |
| EP | 0 269 454 A2 | 6/1988 |
| EP | 0 275 353 A2 | 7/1988 |
| EP | 0 269 324 A2 | 12/1988 |
| EP | 0 300 620 A1 | 1/1989 |
| EP | 0 315 333 A2 | 5/1989 |
| EP | 0 320 814 A2 | 6/1989 |
| EP | 0 322 118 A1 | 6/1989 |
| EP | 0 341 875 A2 | 11/1989 |
| EP | 0 342 950 A2 | 11/1989 |
| EP | 0 355 991 A2 | 2/1990 |
| EP | 0 356 614 A2 | 3/1990 |
| EP | 0 368 541 A1 | 5/1990 |
| EP | 0 375 211 A2 | 6/1990 |
| EP | 0 393 426 A2 | 10/1990 |
| EP | 0 395 215 A1 | 10/1990 |
| EP | 0 475 807 A2 | 3/1992 |
| EP | 0 497 607 A1 | 8/1992 |
| EP | 0 633 757 A1 | 1/1995 |
| EP | 0 633 758 A1 | 1/1995 |
| EP | 0 676 183 A1 | 10/1995 |
| EP | 0 773 764 A1 | 5/1997 |
| EP | 0 855 921 A1 | 8/1998 |
| EP | 0 865 781 A2 | 9/1998 |
| EP | 0 937 792 A1 | 8/1999 |
| EP | 0 955 347 A2 | 11/1999 |
| EP | 1 082 147 A1 | 3/2001 |
| EP | 1 156 838 A1 | 11/2001 |
| EP | 0 782 457 B1 | 12/2001 |
| EP | 1 280 631 | 2/2003 |
| EP | 1 448 128 A2 | 8/2004 |
| EP | 1 452 156 A1 | 9/2004 |
| EP | 1 675 536 A2 | 7/2006 |
| EP | 1 815 875 A1 | 8/2007 |
| EP | 2 001 424 A2 | 12/2008 |
| FR | 1 151 199 | 1/1958 |
| FR | 2 528 695 A1 | 12/1983 |
| FR | 2 531 627 A1 | 2/1984 |
| FR | 2 609 889 | 7/1988 |
| FR | 2 662 361 A1 | 11/1991 |
| GB | 498591 | 1/1939 |
| GB | 713838 | 8/1954 |
| GB | 735972 | 8/1955 |
| GB | 741659 | 12/1955 |
| GB | 781 975 | 8/1957 |
| GB | 307 276 | 1/1959 |
| GB | 819 635 | 9/1959 |
| GB | 821959 | 10/1959 |
| GB | 833587 | 4/1960 |
| GB | 898826 | 6/1962 |
| GB | 950207 | 2/1964 |
| GB | 987 275 | 3/1965 |
| GB | 1018093 | 1/1966 |
| GB | 1049196 | 11/1966 |
| GB | 1110016 | 4/1968 |
| GB | 1203611 | 8/1970 |
| GB | 1282056 | 7/1972 |
| GB | 1390044 | 4/1975 |

(56) References Cited

FOREIGN PATENT DOCUMENTS

| | | |
|---|---|---|
| GB | 1395815 | 5/1975 |
| GB | 1398011 | 6/1975 |
| GB | 1476894 | 6/1977 |
| GB | 1490065 | 10/1977 |
| GB | 1494643 | 12/1977 |
| GB | 1565987 | 4/1980 |
| GB | 2038661 A | 7/1980 |
| GB | 2074029 A | 10/1981 |
| GB | 2081177 A | 2/1982 |
| GB | 2085305 A | 4/1982 |
| GB | 2153229 A | 8/1985 |
| GB | 2170713 A | 8/1986 |
| GB | 2175208 A | 11/1986 |
| GB | 2176401 A | 12/1986 |
| GB | 2186233 A | 8/1987 |
| GB | 2192142 A | 1/1988 |
| GB | 2226780 A | 7/1990 |
| GB | 0606661.7 | 4/2006 |
| GB | 2 423 267 A | 8/2006 |
| GB | 2423267 A | 8/2006 |
| GB | 2 425 487 A | 11/2006 |
| JP | 4312458 A | 11/1992 |
| JP | 10095072 A | 4/1998 |
| JP | 2005-29907 A | 2/2005 |
| JP | 2005-314618 A | 11/2005 |
| SE | 9200983 A | 3/1992 |
| SE | 9200984 A | 3/1992 |
| SE | 9504077 A | 11/1995 |
| WO | WO 87/05206 A1 | 9/1987 |
| WO | WO 88/05269 A1 | 7/1988 |
| WO | WO 90/00732 A1 | 1/1990 |
| WO | WO 90/14109 A1 | 11/1990 |
| WO | WO 91/00718 A1 | 1/1991 |
| WO | WO 91/01706 A1 | 2/1991 |
| WO | WO 91/16059 A1 | 10/1991 |
| WO | WO 92/04923 A1 | 4/1992 |
| WO | WO 92/13576 A1 | 8/1992 |
| WO | WO 93/15249 A1 | 8/1993 |
| WO | WO 93/19709 A1 | 10/1993 |
| WO | WO 93/19710 A1 | 10/1993 |
| WO | WO 94/10953 A1 | 5/1994 |
| WO | WO 94/10957 A1 | 5/1994 |
| WO | 94/17765 | 8/1994 |
| WO | WO 94/20054 A1 | 9/1994 |
| WO | WO 94/21207 A2 | 9/1994 |
| WO | WO 95/30394 A1 | 11/1995 |
| WO | 96/09076 A1 | 3/1996 |
| WO | WO 96/09076 A1 | 3/1996 |
| WO | WO 96/10972 A1 | 4/1996 |
| WO | WO 97/11658 A1 | 4/1997 |
| WO | WO 97/17922 A1 | 5/1997 |
| WO | WO 97/42985 A1 | 11/1997 |
| WO | WO 97/45146 A1 | 12/1997 |
| WO | WO 98/57677 A1 | 12/1998 |
| WO | WO 99/33420 A1 | 7/1999 |
| WO | WO 99/61077 A1 | 12/1999 |
| WO | WO 99/61078 A1 | 12/1999 |
| WO | WO 99/63920 A1 | 12/1999 |
| WO | WO 00/51650 A1 | 9/2000 |
| WO | 00/65143 A1 | 11/2000 |
| WO | 01/68020 A1 | 9/2001 |
| WO | WO 01/85393 A1 | 11/2001 |
| WO | WO 02/20067 A2 | 3/2002 |
| WO | WO 02/28445 A1 | 4/2002 |
| WO | WO 02/28447 A1 | 4/2002 |
| WO | WO 03/039419 A2 | 5/2003 |
| WO | WO 03/079919 A1 | 10/2003 |
| WO | WO 2004/060225 A1 | 7/2004 |
| WO | WO 2004/108175 A1 | 12/2004 |
| WO | 2005/021058 A2 | 3/2005 |
| WO | WO 2005/034797 A2 | 4/2005 |
| WO | WO 2005/058381 A1 | 6/2005 |
| WO | WO 2006/075950 A1 | 7/2006 |
| WO | WO 2006/081403 A1 | 8/2006 |
| WO | WO 2006/127292 A1 | 11/2006 |
| WO | 2007/025544 A1 | 3/2007 |
| WO | WO 2007/113597 A2 | 10/2007 |
| WO | 2008/012443 A2 | 1/2008 |
| WO | WO 2009/047564 A2 | 4/2009 |
| WO | 2010/061228 A1 | 6/2010 |
| WO | WO 2010061228 A1 * | 6/2010 ............... B26D 7/08 |
| WO | 2010/086457 A1 | 8/2010 |
| WO | WO 2012028842 A1 * | 3/2012 ............. A61L 15/26 |
| WO | 2012/104584 A1 | 8/2012 |

OTHER PUBLICATIONS

Starr, The Nonwoven Fabrics Handbook, Association of the Nonwoven Fabrics Industry, Cary, North Carolina, pp. iii-v, 4, 7, 45-62 (Batra et al. eds. 1992).

Colas et al., "Silicone Biomaterials: History and Chemistry & Medical Applications of Silicones," reprinted from Biomaterials Science, $2^{nd}$ Ed., Elsevier, Inc., pp. 80-86 and 697-707 (2005).

Gourlay et al "Physical Characteristics and Performance of Synthetic Wound Dressings," *Trans. Amer. Soc. Artif. Int. Organs* XXI:28-34 (1975).

De Oliveira et al., "Silicone Versus Nonsilicone Gel Dressings: A Controlled Trial," *Dermatol. Burg.* 27:721-726 (2001).

Opposition Against European Patent No. EP 2001424, Opponent Mölnlycke Health Care AB, 28 pages (Aug. 16, 2012).

Declaration of Eric Batelson, Opposition Proceedings regarding EP 2001424, Opponent Mölnlycke Health Care AB, 9 pages (Aug. 14, 2012).

Declaration of Elisabet Lundqvist, Opposition Proceedings regarding EP 2001424, Opponent Mölnlycke Health Care AB, 5 pages (Aug. 14, 2012).

Wacker Silicones, Wacker SilGel® 612, data sheet, 3 pages (2004).

Prisma's Abridged English-Swedish and Swedish-English Dictionary, title page, copyright page, pp. 24, 25, 34, 35 (University of Minnesota Press 1998).

Opposition Against European Patent No. EP 2001424, Opponent 3M Innovative Properties Company, 41 pages (Aug. 22, 2012).

Tan et al., "Pressure-Sensitive Adhesives for Transdermal Drug Delivery Systems," *PSTT* 2(2):60-69 (1999).

Handbook of Technical Textiles, title page, copyright page, pp. 4, 13, 130-151 (Horrocks & Anand eds., 2000).

Wikipedia, "Polydimethylsiloxane," webpage http://en.wikipedia.org/wiki/polydimethylsiloxane, 5 pages (Jun. 6, 2012).

Knovel Plastic Material Data Sheet, Dow Coming 7355 Adhesive, 1 page (Kipp ed., 2004).

Inorganic Polymers, title page, copyright page, pp. 4, 5, 61, 62 (DeJaeger & Gleria eds., 2007).

Handbook of Pressure Sensitive Adhesive Technology, cover page, copyright page, pp. 512-517 (D. Satas ed., 2nd ed. 1989).

Adhesion and Adhesives Technology, The Chemistry and Physical Properties of Elastomer-Based Adhesives, title page, copyright page, pp. 238-241 (A. Pocius ed., 2nd ed. 2002).

Remington: The Science and Practice of Pharmacy, title page, p. 948 (21st ed. 2005).

Thomas, "Silicone Adhesives in Healthcare Applications," Dow Corning Healthcare Industry, 6 pages (2003).

Sample Preparation Handbook for Transmission Electron Microscopy, Introduction to Materials, title page, copyright page, pp. 12-13 (Ayache et al. eds., 2010).

"Tendra Startpage>Products>Safetec Technology," Screenshots of archived webpage http://www.tendra.com/item.asp?id=1015&lang=2, Internet Archive: Wayback Machine, 6 pages (Nov. 23, 2003).

"Tendra Startpage>Products>Safetec Technology>Silicone," Screenshots of archived webpage http://www.tendra.com/bottom.asp?id=1869&lang=2, Internet Archive: Wayback Machine, 3 pages (May 5, 2003).

"Tendra Startpage>Products> Safetec Technology>Dressings," Screenshots of archived webpage http://www.tendra.com/bottom.asp?id=1021&lang=2, Internet Archive: Wayback Machine, 8 pages (May 3, 2003).

"Tendra Startpage>Products>Alphabetical List>Multiplex®Border," Screenshots of archived webpage http://

(56) References Cited

OTHER PUBLICATIONS www.tendra.com/item.asp?id=774&pid=558, Internet Archive: Wayback Machine, 3 pages (May 11, 2003).
Tendra, Mepilex® Border Product Sheet, 2 pages (accessed via Internet Archive: Wayback Machine, archived webpage http://www.tendra.com/item.asp?id=774&pid=558, Related Links, Product Sheet) (May 11, 2003).
David D. Johnson, Ph.D., Analytical Report Concerning MEPILEX™ Border Product from Manufacture Lot 3894-01F18, Opposition Proceedings regarding EP 2001424, Opponent 3M Innovative Properties Company, 16 pages (Jul. 6, 2012).
Declaration of David R. Holm, Opposition Proceedings regarding EP 2001424, Opponent 3M Innovative Properties Company, 1 page (Aug. 17, 2012).
Declaration of David D. Johnson, Opposition Proceedings regarding EP 2001424, Opponent 3M Innovative Properties Company, 1 page (Aug. 12, 2012).
Declaration of Clas Bolander, MSc, Sourcing Director, Wound Care Division, Mölnlycke Health Care AB, Opposition Proceedings regarding EP 2001424, Opponent 3M Innovative Properties Company, 1 page (Aug. 13, 2012).
Opposition Against European Patent No. EP 2001424, Opponent Lohmann & Rauscher GmbH & Co. KG, 23 pages (Aug. 23, 2012).
Thomas, "World Wide Wounds-Atraumatic Dressings," www.worldwidewounds.com/2003/january/Thomas/Atraumatic-Dressings.html, 11 pages (2003).
Declaration of Stephen Thomas, Ph.D., Opposition Proceedings regarding EP 2001424, Opponent Lohmann & Rauscher GmbH & Co. KG, 54 pages (Aug. 20, 2012).
Medika AG, Mölnlycke Health Care, price list, 2 pages (2004).
Davies, "Milestones in the Management of Wound Trauma and Pain," Poster Presentation, European Wound Management Association Conference, Glasgow, United Kingdom (2007).
D.E. Packham, Packham Handbook of Adhesion, title page, copyright page, pp. 25-27, 363-365 (2nd ed. 2005).
Handbook of Adhesive Technology, title page, copyright page, pp. 847-848 (Pizzi & Mittal eds., 2003).
Polymer Science, Inc., "Medical," webpage http://www.polymerscience.com/medical.html, 2 pages (Accessed Aug. 17, 2012).
Thomas, X., "Silicones in Medical Applications," Chapter 2.17 in Inorganic Polymers, 12 pages (De Jaeger & Gleria eds., 2007).
Benedek & Heymans, Pressure Sensitive Adhesives Technology, cover page, copyright page, p. 128 (1997).
Declaration of Dr. Thomas Pontzen, Opposition Proceedings regarding EP 2001424, Opponent Lohmann & Rauscher GmbH & Co. KG, 2 pages (Aug. 23, 2012).
Opposition Against European Patent No. Ep 2001424, Opponents Gerhard Schmitt-Nilson, Stefan Waibel, 37 pages (Aug. 23, 2012).
Thomas & Mitchell, "Adhesive Technologies for Attaching Medical Devices to the Skin," *Medical Device Technology*, pp. 12-15 (Sep. 2004).
Quinn, "Silicone Gel in Scar Treatment," *Burns* 13:S33-S40 (1987).
Musgrave et al., "The Effect of Silicone Gel Sheets on Perfusion of Hypertrophic Burn Scars," *Journal of Burn Care and Rehabilitation* 23(3): 208-214 (2002).
Wikipedia, "Pressure-Sensitive Adhesive," webpage http://en.wikipedia.org/w/index.php?title=Pressure-sensitive_adhesive&oldid=499251304, 4 pages (Jun. 25, 2012).
Wacker Chemie AG, "Wacker SilGel®, The Specialist for Sensitive Devices," 1 page (2012).
Joe McMahon, M.SC., "Microstructural and Chemical Characterization of Mepilex Border Wound Dressing," Report, Opposition Proceedings regarding EP 2001424, Opponents Gerhard Schmitt-Nilson, Stefan Waibel, 11 pages (Aug. 20, 2012).
Kirit Amin, "Characterization of Mepilex Border by 1H NMR Spectroscopy," Report, Opposition Proceedings regarding EP 2001424, Opponents Gerhard Schmitt-Nilson, Stefan Waibel, 6 pages (Aug. 22, 2012).
Amazon.Com, "ScarAway Professional Grade Silicone Scar Treatment Sheets," webpage, 2 pages (Aug. 20, 2012).
Mitchell-Vance Laboratories, "ScarAway®: The Solution for Scars™," webpage http://www.scaraway.us, product information, 1 page (Aug. 23, 2012).
ACNE4IDIOTS.Com, "ScarAway Professional Grade Silicone Scar Treatment Sheets," webpage, 4 pages (Aug. 23, 2012).
Epinions.Com, "Neosporin Scar Solution Silicone Scar Sheets 28 Each," webpage, 3 pages (Aug. 23, 2012).
Opposition Against European Patent No. EP 2001424, Supplement to Facts and Submissions of Notice of Opposition, Opponents Gerhard Schmitt-Nilson, Stefan Waibel, 4 pages (Oct. 29, 2012).
Kirit Amin, "Characterization of Mepilex Border by 1H NMR Spectroscopy," Supplemental Report, Opposition Proceedings regarding EP 2001424, Opponents Gerhard Schmitt-Nilson, Stefan Waibel, 11 pages (Aug. 2012).
Joe McMahon, M.SC., "Microstructural and Chemical Characterization of Silicone Scar Sheet," Interim Report, Opposition Proceedings regarding EP 2001424, Opponents Gerhard Schmitt-Nilson, Stefan Waibel, 5 pages (Sep. 11, 2012).
Kirit Amin, "NMR Report on Characterization of Silicone Scar Sheet," Supplemental Report, Opposition Proceedings regarding EP 2001424, Opponents Gerhard Schmitt-Nilson, Stefan Waibel, 10 pages (Sep. 2012).
Joe McMahon, M.SC., "Chemical Characterization of Glue and Polymer Layers in Wound Dressings," Final Report, Opposition Proceedings regarding EP 2001424, Opponents Gerhard Schmitt-Nilson, Stefan Waibel, 10 pages (Oct. 2, 2012).
Opposition Against European Patent No. EP 2001424, Response to Request for Documents, Opponents Lohman & Rauscher GmbH & Co. KG, 2 pages (Oct. 29, 2012).
McCulloch, "The History of the Development of Melt Blowing Technology," *International Nonwovens Journal*, 11 pages (1999).
Bresee & Ko, "Fiber Formation During Melt Blowing," *INJ Summer*, pp. 21-28 (2003).
Farer et al., "Study of Meltblown structures Formed by Robotic and Meltblowing Integrated System: Impact of Process Parameters on Fiber Orientation," *INJ Winter*, pp. 14-21 (2002).
Zhao, "Melt Blown Dies: A Hot Innovation Spot," *INJ Winter*, pp. 37-41 (2002).
Prof. W. Woebcken, Kunststoff Lexicon, title page, copyright page, pp. 418-419 (1998).
"Milestones in Our History," Screenshot of Mölnlycke Health Care webpage http://www.molnlycke.com/au/About-us/The-Company/AUSNZ/History/Milestones-in-our-History/, 1 page (Aug. 23, 2012).
A. Vasel-Biergans & W. Probst, Wundauflagen für die Kitteltasche, 4 pages (2nd ed. 2006).
Gantner et al., "Soft Skin Adhesive Gels and Liners: New Formulating Options for Tailored Solutions," Dow Corning Corporation (2007).
PCT International Search Report and Written Opinion for PCT/GB2009/050500 (Jul. 22, 2009).
United Kingdom Intellectual Property Office, Search Report for Application No. GB0908057.3 (Sep. 4, 2009).
PCT International Search Report and Written Opinion for PCT/GB2007/050179 (Aug. 21, 2008).
Ulman & Thomas, "Silicone Pressure Sensitive Adhesives for Healthcare Applications" in Handbook of Pressure Sensitive Adhesive Technology-2, Ch. 6, pp. 133-157 (D. Satas ed. 1995).
Blackwood, "Achieving Functional Excellence with Silicone Coatings," Dow Corning Corporation, 8 pages. (2004).
Dow Corning® 7-9700 Soft Skin Adhesive Kit (A&B) Product Description, Typical Properties, https://www.dowcorning.com/applications/search/products/Details.aspx?prod=04035943&type=prod, 1 page (retrieved Jan. 6, 2016).
Dow Corning® 7-9800 Soft Skin Adhesive Kit (A&B) Product Description, Typical Properties, http://www.dowcorning.com/applications/search/default.aspx?R=1059EN, 1 page (retrieved Jan. 6, 2016).
Viscosity Tables, V&P Scientific Inc, http://www.vp-scientific.com/Viscosity_Tables.htm, 3 pages (retrieved Jan. 6, 2016).

\* cited by examiner

NON-ADHERENT WOUND DRESSING

This application claims the benefit of UK Patent Application No. 1114718.8, filed Aug. 25, 2011, which is hereby incorporated by reference in its entirety.

FIELD OF THE INVENTION

This invention relates to a non-adherent wound dressing, and in particular to such a wound dressing comprising a non-adherent silicone gel as skin- or wound-contact material.

BACKGROUND OF THE INVENTION

Different types of wound dressing are required to meet different clinical needs. However, there are several desirable characteristics that are common to all wound dressings. Pain-free removal and the ability to remove a dressing without trauma to the wound and the surrounding skin are two of the most important characteristics. In order to prevent pain and trauma, the facing layer of a wound dressing needs to maintain a moist layer over the wound to prevent adherence to the drying wound. However, it is also desirable for a wound dressing to include some form of adhesive layer to maintain it in position. Island dressings are typically used, which comprise a so-called "non-adherent" or "low-adherent" absorbent pad with an adhesive retention layer over the top forming an adhesive border that sticks to skin surrounding the wound. However, repeated removal and replacement of such dressings can damage the peri-wound skin, ie the wound adjacent to the skin. The term "atraumatic dressing" is used in relation to products that, upon removal, do not cause trauma either to newly formed tissue or to the peri-wound skin.

There is an ongoing need to provide improved wound dressings. No single wound dressing product is suitable for use in all wound types or at all stages of healing.

Hydrophobic silicone gels of the type referred to as soft silicones adhere readily to dry skin but do not stick to the surface of a moist wound and do not cause damage on removal. As well as satisfying these principal requirements for use as the skin contact layer in atraumatic dressings, there are several other intrinsic properties of soft silicone that make it particularly advantageous for use in wound dressings. These properties are well-documented and include the fact that silicones are non-toxic, non-allergenic or -sensitising, feel soft on the skin and are conformable yet robust.

Numerous published papers describe the properties of silicone and the use of soft silicone dressings. Indeed, there are different types of soft silicone dressings currently on the market, including atraumatic wound contact layers, absorbent dressings for exuding wounds and also a dressing for the treatment of hypertrophic scars and keloids.

EP-A-0633757 is concerned with methods by which a dressing comprising a perforated carrier coated with silicone can be manufactured. That method involves blowing cold air onto the underside of the carrier to prevent silicone clogging the perforations. The carriers that are described are plastic films, and the document discusses the need to ensure good adherence between the silicone gel and the carrier. Measures such as the application of silicone primer, the use of microporous carrier films, and the use of a two-ply carrier comprising a plastic film laminated to a non-woven or textile material are suggested as ways of achieving this objective.

WO-A-2007/113597 describes laminates suitable for incorporation into wound dressings, which comprise a structural layer coated on one side with silicone gel and on the other with a pressure-sensitive adhesive such as an acrylic adhesive. Melt-blown polyurethane is used as the structural layer.

An absorbent dressing made from polyurethane foam is sold under the trade name Mepilex®. The outer surface of the foam is bonded to a vapour-permeable polyurethane membrane that acts as a barrier to liquids and micro-organisms. The inner surface of the foam is coated with a layer of soft silicone.

An absorbent, self-adhesive island dressing with a perforated soft silicone wound contact layer is sold under the trade name Mepilex Border®. The absorbent core consists of three components: a thin sheet of polyurethane foam, a piece of non-woven fabric, and a layer of super-absorbent polyacrylate fibres.

Another commercially available product, sold under the trade name Mepilex Transfer®, consists of a thin sheet of a hydrophilic open-cell polyurethane foam, coated on one surface with a layer of soft silicone and presented on a plastic film carrier.

The product sold under the trade name Mepitel® is a porous, semi-transparent wound contact layer consisting of a flexible polyamide net coated with soft silicone. This product is as described in EP-A-0261167, which describes an elastic, hydrophobic, knitted network coated with silicone gel. The structure of the knitted network provides openings that are not occluded by the silicone, and which thereby permit the passage of wound exudate in use.

The Mepitel® product has proven to be useful in many circumstances, but it does suffer from certain disadvantages. For example, production of the net to which the silicone is applied, which is done by warp knitting, is a relatively complex process, which is not amenable to the production of materials with widely differing sizes of opening. Also, because the knitted substrate is produced using a polyamide yarn, there is a danger of the product shedding fibre during use, which could contaminate the wound to which it is applied. A particular disadvantage of such products, however, is that they are of essentially fixed dimensions, with very little extensibility in any direction. This means that they do not conform well to the surface of an irregularly-shaped part of the body, eg a knee, with the result that when applied to such an area they may not remain in position and may be easily dislodged. A further disadvantage is that retention of the silicone gel on the substrate depends on the silicone fully encapsulating the substrate; failure of the silicone to fully encapsulate the substrate at any point might create a point of weakness at which the silicone may separate from the substrate, thereby impairing the performance of the product and/or leading to undesirable loss of silicone into the wound.

The present invention is directed to overcoming these and other deficiencies in the art.

SUMMARY OF THE INVENTION

According to a first aspect of the invention there is provided a non-adherent wound dressing comprising a substrate in the form of a perforated sheet of melt-blown non-woven material, the substrate being impregnated with, and coated on both sides with, a silicone gel.

According to a second aspect of the invention, there is therefore provided a method for the manufacture of a non-adherent wound dressing, which method comprises
 a) providing a sheet of melt-blown non-woven material;
 b) applying to the sheet a silicone gel precursor composition, such that the sheet is impregnated with the composition and coated on both sides with the composition; and c) causing or allowing the silicone gel precursor composition to cure, thereby forming a silicone gel.

There has now been devised a non-adherent wound dressing comprising a silicone gel skin- or wound-contact material, which overcomes or substantially mitigates some or all of the above-mentioned and/or other disadvantages of the prior art.

DETAILED DESCRIPTION OF THE INVENTION

Figure 1:
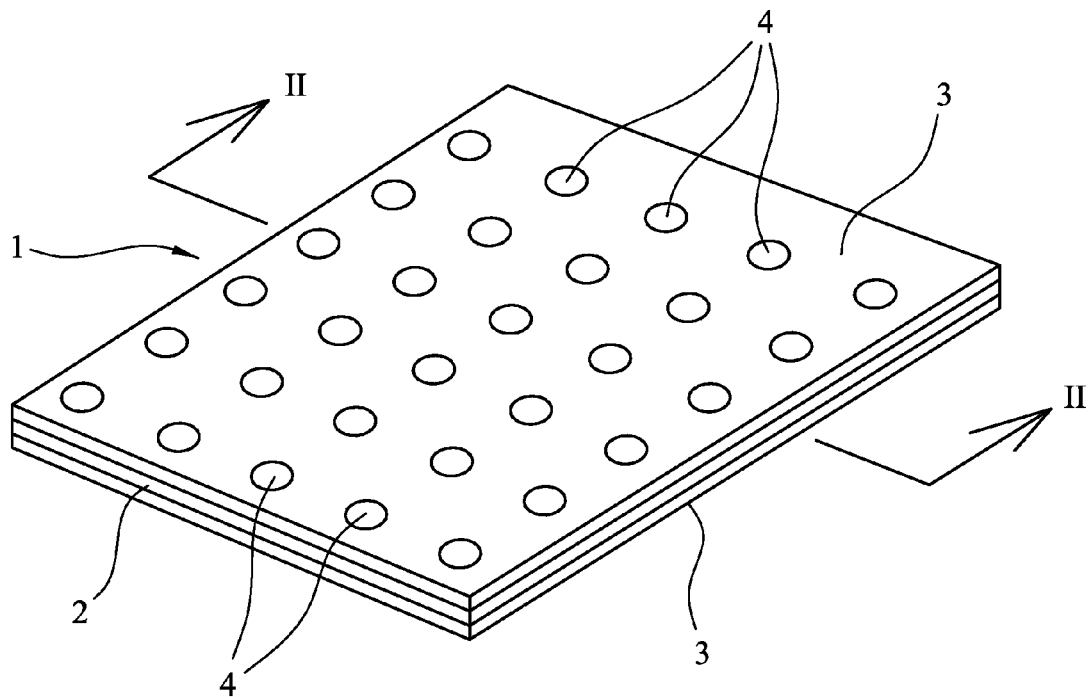
FIG. 1 is a perspective view of a non-adherent wound dressing according to the invention.

According to a first aspect of the invention there is provided a non-adherent wound dressing comprising a substrate in the form of a perforated sheet of melt-blown non-woven material, the substrate being impregnated with, and coated on both sides with, a silicone gel.

The dressing according to the invention is advantageous for a number of reasons. First, the substrate, being of a melt-blown non-woven material, is readily extensible in all directions, enabling the dressing to be stretched and so facilitating its secure application, even to irregularly shaped parts of the body. Secondly, because the substrate is impregnated with the silicone gel, the silicone is securely fixed to the substrate, minimising the likelihood of silicone being separated from the dressing during use. Because the melt-blown material of the substrate is non-fibrous, there is no risk of loss of fibrous material into the wound to which the dressing is applied in use. The dressing may also be readily manufactured, and the size of the perforations in the substrate can be easily varied.

By "non-adherent" in this context is meant that the wound dressing can be removed after application to a wound without causing significant disruption or trauma to the wound or to the surrounding skin. The dressing may nonetheless be somewhat tacky so that it holds its position once applied to the wound.

The substrate is a sheet of melt-blown non-woven material. A wide range of suitable non-woven materials are commercially available, from a variety of suppliers. Melt-blown non-wovens are typically produced by extruding melted polymer fibres through a spin net or die having up to 16 holes per centimeter to form long thin fibres which are stretched and cooled by passing hot air over the fibres as they fall from the die. Commonly, the fibres are deposited on a cooled conveyor where they agglomerate into a fused web yet retain their fibrillar form such that the resultant product has an irregular open structure. The web is collected into rolls.

Melt-blown non-woven materials may be produced using a variety of polymers, including polyolefins such as polypropylene. A particularly preferred material for use in the present invention, however, is melt-blown polyurethane (MBPU).

In most embodiments, the dressing of the invention consists only of the substrate, eg of MBPU, and the silicone gel that is impregnated into and coats the substrate.

The silicone gel that is suitable for use in the present invention will generally be hydrophobic and may be tacky or non-tacky. Generally, for most applications, tacky silicone gels are preferred as they cause the wound dressing to be retained in position when applied, yet are non-adherent. Such silicone gels are of the kind often referred to as soft silicone.

Most preferably, suitable silicone gels are formed by reaction between two components that are mixed to form a silicone gel precursor composition, immediately prior to application to the substrate. Suitable components that are intended for such reaction to form a silicone gel are readily available commercially. Typically, the two components are a vinyl-substituted silicone and a hydride-containing silicone. The precursor composition cures to form the silicone gel. Many such compositions will cure at room temperature, but generally curing is brought about or accelerated by heating.

Gels having different properties may be produced by varying the proportions and/or nature of the components used in the reaction. For example, the molecular weights of the various components and/or their degree of substitution by reactive groups may be different.

Suitable components for forming silicone gels for use in the dressing of the present invention are readily available.

The silicone gel may be coated onto the substrate at a wide variety of coating weights. The most appropriate coating weight will depend on the properties of the gel and its intended application. Typically, the gel may be applied to the substrate at a weight of between 50 g/m$^2$ and 800 g/m$^2$. The thickness of the gel coating on each side of the substrate may typically be between 5 µm and 10 mm, more commonly between 20 µm and 5 mm.

Most conveniently, the silicone gel (or, more accurately, the precursor composition that reacts to form the gel) is applied to the substrate by a dipping process, in which the substrate is introduced into, or transported through, a bath containing the mixture of precursor components. The bath is preferably continuously replenished with precursor composition. Such a process lends itself to a continuous, rather than batch, production process. Other methods of application may, however, alternatively be used.

The substrate of the dressing according to the invention is perforated. The purpose of the perforations is to permit fluid, notably wound exudate and the like, to be transmitted through the dressing. The perforations may, however, also provide for ease of removal of the dressing, improved flexibility and conformity, and skin breathability.

The perforations may be formed after application of the silicone gel to the substrate. In such a case, the silicone gel precursor composition will be applied to substrate and caused to cure, and then the perforations may be formed, eg by one of the methods described below. More preferably, however, the perforations are formed in the substrate, prior to application of the silicone precursor composition, the silicone precursor composition is applied to a perforated substrate. In any event, it is generally desired that the perforations should not be occluded by the silicone gel (since otherwise fluid would not be able to pass through them). In such cases, variables such as the nature of the silicone precursor composition, the quantity of silicone precursor composition that is applied, the size of the perforations etc, are all controlled in such a way that the perforations are not occluded.

In one group of presently preferred embodiments of the invention, the substrate is formed with a regular array of perforations. Typically, such perforations are circular and have a diameter of from 50 µm to 10 mm, more commonly from 1 mm to 5 mm. Other shapes of perforation may alternatively be used, eg square perforations or elongated slits. Some such arrangements of perforations may enhance the extensibility of the dressing in one or more directions, and so improve its conformability to the body.

Irrespective of whether the perforations are formed before or after application of the silicone composition to the substrate, they may be produced by mechanical cutting, eg using a rotary or reciprocating cutting die.

A currently preferred method of forming the perforations, however, involves the application of high frequency mechanical vibrations in a similar manner to ultrasonic welding technology. Again, the perforations may be formed either before or after application of the silicone gel precursor composition to the substrate, but it is presently preferred that the perforations be formed in the substrate prior to application of the precursor composition. This method involves contacting perforating elements with the coated or uncoated substrate sheet and subjecting the sheet, at least in the regions contacted with the perforating elements, to high frequency mechanical vibrations.

The application of high frequency mechanical vibrations to the sheet brings about the generation of localised heat by friction, which leads to softening of the material, thereby facilitating puncturing of the material by the perforating elements.

The high frequency mechanical vibrations are preferably applied to the material using a device of the type commonly used in ultrasonic welding. These devices are typically used to weld thermoplastic or fine metal components by applying high frequency mechanical vibrations to such components as they are held together under pressure. This combination of mechanical vibration and pressure results in the generation of heat by friction, allowing the generation of heat to be localised to the points at which the material is held under pressure. The use of ultrasonics is of particular advantage in the medical industry because it does not introduce potential contaminants into the material. The use of ultrasonics is advantageous compared to the direct application of heat to the material because it is highly controllable and may be switched off instantaneously without any residual effect. Excess or residual heat is undesirable because it may damage the substrate or cause it to deform. Also, the effects of ultrasonics can be restricted to a very limited part of the material without altering the properties of the surrounding regions. Ultrasonic techniques have previously been used for the formation of perforations in a variety of materials, including sheet materials intended for use as components of wound dressings.

The sheet material is generally held between the perforating elements and a sonotrode, by which the high frequency vibrations are applied. The perforating elements preferably take the form of a plurality of projections extending from a support, such that the tips of the perforating elements contact the sheet material. The sonotrode may then be applied to the other side of the material so as to hold the sheet material under pressure between the sonotrode and the support, compressing the sheet material between the sonotrode surface and the projections at the points at which it is in contact with the tips of those projections. The generation of heat by friction is thereby localised to the points of the sheet material that are in contact with the tips of the perforating elements. The perforating elements may then pass through the sheet material at these points, producing perforations. The perforating elements thereby serve to compress the sheet against the sonotrode at the desired points, localising the generation of heat to the points at which they contact the sheet, followed by perforation of the sheet at those points.

The perforating elements most preferably pierce the sheet as soon as possible following contact with the sonotrode. It is therefore desirable to apply a force to the sheet to facilitate passage of the perforating elements through the laminate. This may be done by applying suction, by holding the sheet under tension against the perforating elements, or by applying a mechanical force directly to the sheet.

The support from which the perforating elements extend preferably takes the form of a roller with the perforating elements extending from its circumferential surface. Such a roller will typically have a diameter of between 5 cm and 50 cm, more commonly between 10 cm and 30 cm. The sheet may be fed on and off the roller and make contact with the sonotrode continuously, improving throughput. The sonotrode must therefore apply high frequency mechanical vibrations to the material continuously. It is therefore necessary to supply the high frequency mechanical vibrations to the sonotrode using a continuous pulsating generator, rather than an intermittent pulsating generator, both of which are commonly used in the field of ultrasonics.

Generally, operation of the sonotrode for continuous periods will, unless appropriate measures are put in place to maintain the temperature of the sonotrode at a substantially constant level, result in the generation of heat and an increase in the temperature of the sonotrode. This can lead to thermal expansion of the sonotrode, which may reduce the clearance between the sonotrode and the perforating elements. It may therefore be desirable or necessary for the sonotrode to be cooled during operation, eg by the application of a cooling fluid, most commonly chilled air.

The sheet on which the process is carried out is typically in the form of an elongate strip with a width that generally does not exceed 200 mm, although the use of strips with greater widths is possible. However, sonotrodes having a width of greater than about 200 mm are less effective at applying high frequency mechanical vibrations to a material. Therefore, in order to perforate strips of material having widths in excess of 200 mm, a number of sonotrodes positioned adjacent to one another may be used.

The sheet is preferably fed past the perforating elements at a rate of at least 0.1 meters/second and up to 1.0 meters/second. Typically, the sheet may be fed through the apparatus at a rate of between 0.2 and 0.8 meters/second, or between 0.3 and 0.6 meters/second.

According to a second aspect of the invention, there is therefore provided a method for the manufacture of a non-adherent wound dressing, which method comprises
a) providing a sheet of melt-blown non-woven material;
b) applying to the sheet a silicone gel precursor composition, such that the sheet is impregnated with the composition and coated on both sides with the composition; and
c) causing or allowing the silicone gel precursor composition to cure, thereby forming a silicone gel.

In currently preferred embodiments of the invention, the sheet of melt-blown non-woven material to which the silicone gel precursor composition is applied is a perforated sheet. In other embodiments, perforations are formed in the sheet after application of the silicone gel precursor composition, most commonly after curing to form the silicone gel has taken place.

Manufactured dressings according to the invention will generally be packaged as individual units in envelopes that are bacteria-proof and which are sterilized, most commonly using ethylene oxide or by irradiation with γ-radiation.

The dressing will most commonly be supplied with release liners applied to each side. The release liners are removed to expose the silicone gel in use. The release liners are most preferably formed in such a way as to be readily grasped and removed, eg by having one or more projecting tabs.

Embodiments of the invention will now be described in greater detail, by way of illustration only, with reference to the accompanying drawings.

Figure 2:
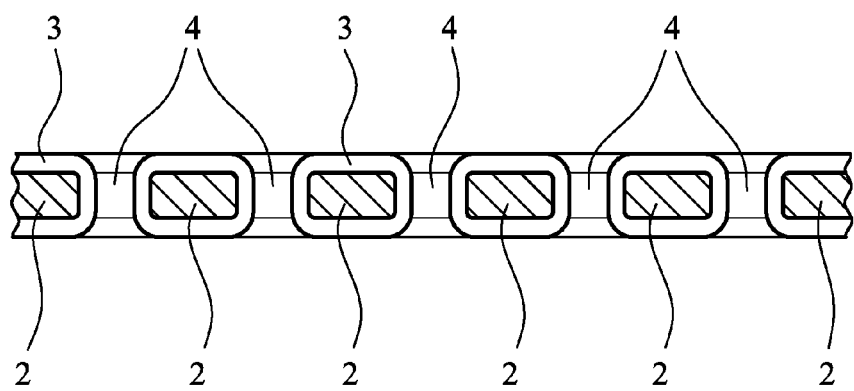
FIG. 2 is a cross-sectional view on the line II-II in FIG. 1.

Referring first to FIGS. 1 and 2, a non-adherent wound dressing according to the invention is generally designated 1 and comprises a sheet of melt-blown polyurethane (MBPU) 2 that is impregnated, and coated on both sides, with a tacky silicone gel 3. The dressing 1 is rectangular in form, with dimensions 5×7 cm. Any one of a wide range of other sizes is of course possible, eg 5×7 cm, 8×10 cm, 12×15 cm, 20×30 cm or 35×60 cm. Other shapes are also possible, including square dressings, circular dressings, elliptical dressings, and dressings specially shaped for application to particular areas of the body, eg limbs or the sacrum.

The sheet 2 of MBPU is perforated, having a regular array of circular perforations 4. The perforations 4 are of such a size that they are not occluded by the silicone gel 3, such that the dressing 1 as a whole is perforated. In the illustrated embodiment, the perforations 4 are approximately 3 mm in diameter, but larger and smaller perforations may alternatively be used and may be appropriate for particular applications.

Figure 3:
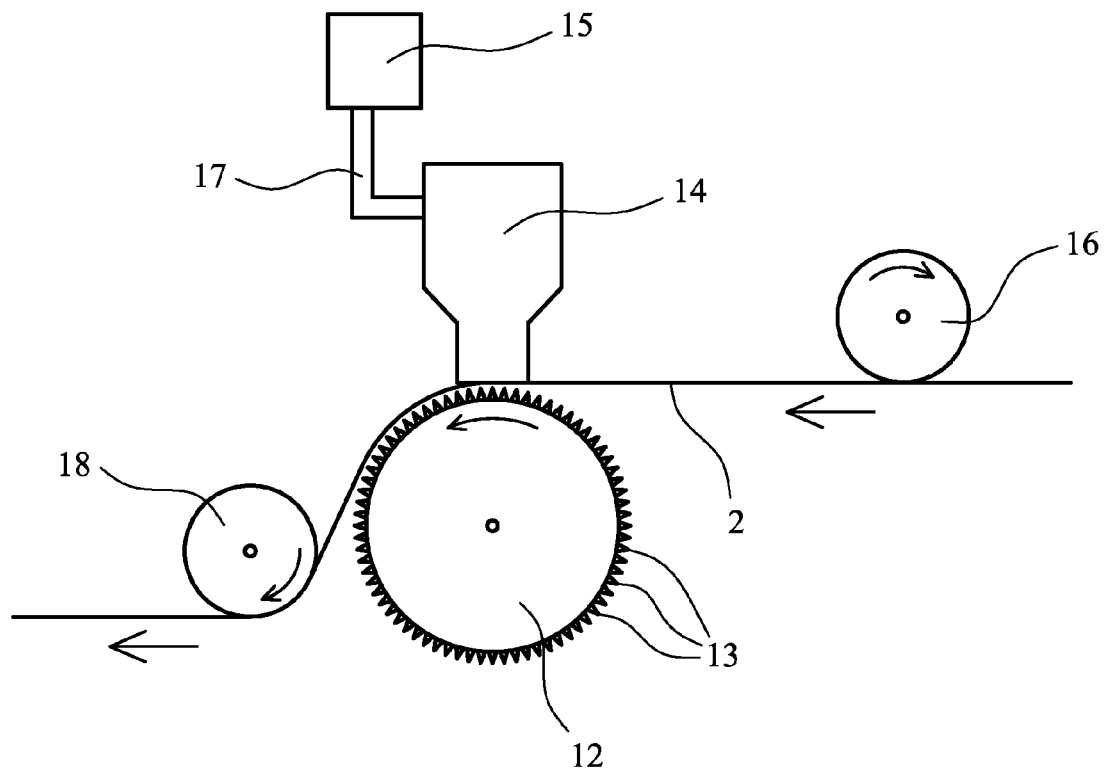
FIG. 3 is a schematic representation, not to scale, of apparatus used to produce perforations in a sheet of melt-blown non-woven material forming part of the dressing of FIGS. 1 and 2.

Turning now to FIG. 3, apparatus is depicted by which the perforations 4 are introduced into the MBPU material 2. The perforating apparatus consists of a perforating roller 12 which is a cylindrical barrel having a multitude of flat-tipped, pin-like perforating elements 13 projecting from the circumferential surface, and a sonotrode 14 which, in operation, applies high frequency mechanical vibrations to the MBPU material 2. The perforating roller 12 and sonotrode 14 are configured such that when the perforating roller 12 is rotated, the tips of the perforating elements 13 pass close to the surface of the sonotrode 14. The diameter of the perforating roller 12 is approximately 20 cm, and the perforating elements 13 have a length of approximately 5 mm.

In operation, the sheet 2 of MBPU is drawn past a guide roller 16 into the nip between the perforating roller 12 and the sonotrode 14. The points at which the sheet 2 contacts the tips of the perforating elements 13 of the perforating roller 12 are compressed against the surface of the sonotrode 14. The high frequency mechanical vibrations produced by the sonotrode 14 generate high levels of friction at the points where sheet 2 is compressed, causing heating of the sheet 2 at these points. The material of the sheet 2 melts at those points were such heating occurs, allowing the perforating elements 13 to pass through the sheet 2, thereby forming the perforations 4.

The perforated sheet 2 is drawn off the perforating roller 12 via a second guide roller 18. The second guide roller 18 is positioned such that the sheet 2 remains in contact with the surface of the perforating roller 12 after passing through the nip between the perforating roller 12 and the sonotrode 14. This means that the locally heated material of the sheet 2 cools somewhat before being drawn off the perforating roller 12 and the perforating elements 13 are withdrawn from the perforations 4 that have been formed, so that the integrity of the perforations 4 is maintained.

Chilled air from a chiller unit 15 is blown through the sonotrode 14 via a conduit 17. The flow of chilled air is controlled to maintain the temperature of the sonotrode 14 substantially constant, and hence prevent thermal expansion of the sonotrode 14 that would otherwise reduce the clearance between the sonotrode 14 and the tips of the perforating elements 13.

The sheet 2 is drawn off the perforating roller 12 at a rate of approximately 0.3 meters/second. The perforated sheet 2 may be taken up on a roller (not shown) for storage or may pass directly to further processing stations as described below.

Figure 4:
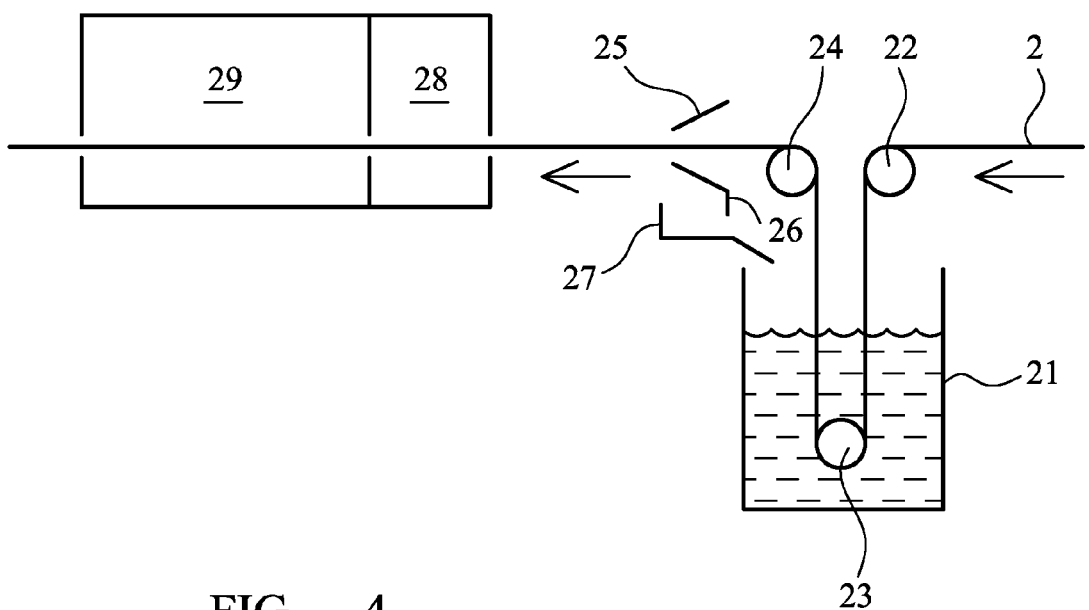
FIG. 4 is a schematic representation of apparatus used in the impregnation and coating of the perforated melt-blown non-woven material.

Turning now to FIG. 4, apparatus is schematically depicted for the impregnation and coating of the perforated MBPU sheet 2 with silicone gel. The apparatus comprises a bath 21 into which the two components of a conventional silicone gel precursor composition are continuously fed. The two components may be fed to the bath 21 via separate inlets or, more conveniently, the two components may be mixed in an appropriate proportion in a mixing head from which the mixed composition is discharged to the bath 21.

The perforated MBPU sheet 2 is conveyed through the bath 21 via a series of guide rollers 22,23,24. The rate of travel of the sheet 21 through the bath 21, and the depth of the composition in the bath 21 (and hence the contact time between the sheet 2 and the composition) are chosen to achieved the desired degree of impregnation and coating of the sheet 2. Any excess composition is removed from the sheet 2 as it exits the bath 21 by an arrangement of wiper blades 25,26 and a drip tray 27 from which any collected composition drains back into the bath 21.

The impregnated and coated sheet 2 next enters a first curing stage 28 where it passes beneath a bank of medium wave infra-red heaters that operate continuously. The thermal energy from these heaters initiates curing of the silicone mixture, and in particular cures the upper surface of the mixture, which maintains the structural integrity of the silicone layer during passage of the coated sheet 2 through a second, longer curing stage 29. In the second curing stage 29, the coated sheet 2 passes beneath further medium wave infra-red heaters. Curing of the silicone mixture, to form a layer of gel of the desired thickness and other properties, is completed during passage of the sheet 2 through the second curing stage 29. The operating parameters may be optimised to suit the particular product being manufactured. Variables that may be adjusted include the power of the infra-red heaters, the speed of passage through the various stages of the process, as well as the length of the curing stages. Typically, the time taken for the laminate to pass through the curing stages is between 5 and 15 minutes.

After curing of the silicone to form the silicone gel coating 3 on the sheet 2, dressings according to the invention are formed by cutting out of individual dressings from the coated and impregnated sheet 2. Most conveniently, release liner material is applied to both sides of the sheet 2 prior to cutting, so that the individual dressings 1 are formed with release liners applied to both sides. The individual dressings are then packaged, and the packages sterilised.

Figure 5:
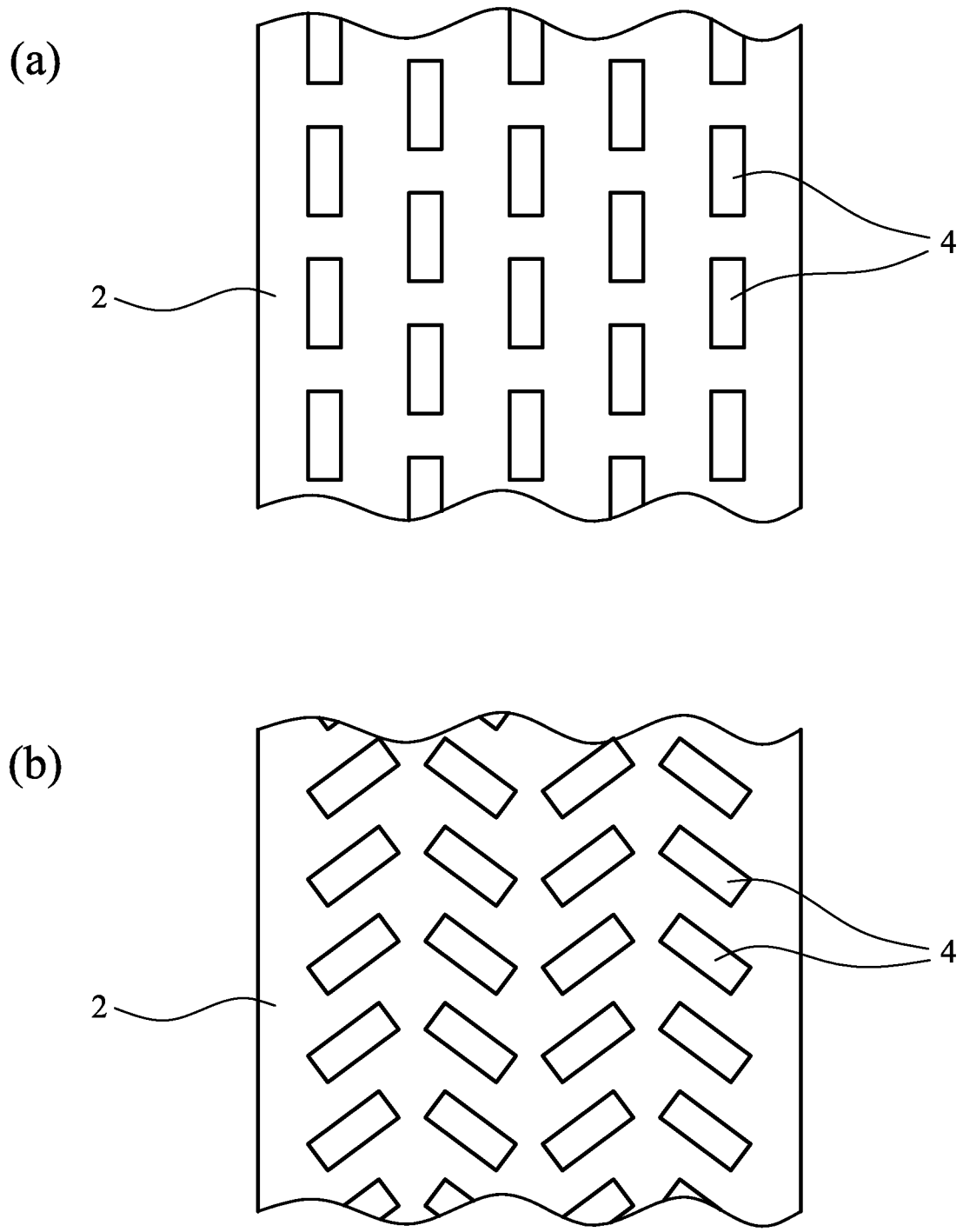
FIG. 5 shows alternative patterns of perforations that may enhance the extensibility of the dressing, and hence its conformability to the body.

Finally, FIG. 5 shows two alternative arrangements of perforations that may enhance the extensibility of the dressing, and hence its conformability to the body. In FIG. 5(a), the perforations are elongate slots arranged in parallel, staggered rows, while in FIG. 5(b) the perforations are elongate slots arranged in a herringbone pattern.

Although preferred embodiments have been depicted and described in detail herein, it will be apparent to those skilled in the relevant art that various modifications, additions, substitutions, and the like can be made without departing from the spirit of the invention and these are therefore considered to be within the scope of the invention as defined in the claims which follow.

What is claimed:

1. A non-adherent wound dressing consisting of a substrate in the form of a perforated sheet of melt-blown non-woven material, the substrate being impregnated with, and coated on both sides with, a silicone gel, wherein the non-adherent wound dressing is readily extensible in all directions, and wherein said non-adherent wound dressing can be stretched to facilitate application of said dressing to irregularly shaped parts of the body.

2. A dressing as claimed in claim 1, wherein the substrate comprises melt-blown polyurethane.

3. A dressing as claimed in claim 1, wherein the silicone gel is a tacky silicone gel.

4. A dressing as claimed in claim 1, wherein the silicone gel is present at a weight of between 50 g/m$^2$ and 800 g/m$^2$.

5. A dressing as claimed in claim 1, wherein the thickness of the gel coating on each side of the substrate is between 5 μm and 10 mm.

6. A dressing as claimed in claim 5, wherein the thickness of the gel coating on each side of the substrate is between 20 μm and 5 mm.

7. A dressing as claimed in claim 1, wherein the perforated sheet comprises a regular array of perforations.

8. A dressing as claimed in claim 7, wherein the perforations are circular and have a diameter of from 50 μm to 10 mm.

9. A dressing as claimed in claim 8, wherein the perforations are circular and have a diameter of from 1 mm to 5 mm.

10. A method for the manufacture of a non-adherent wound dressing, which method comprises
    a) providing a sheet of melt-blown non-woven material;
    b) applying to the sheet a silicone gel precursor composition to impregnate the sheet with the composition and coat the sheet on both sides with the composition; and
    c) curing the silicone gel precursor composition to form said non-adherent wound dressing consisting of the sheet impregnated with and coated on both sides with a silicone gel,
    wherein said non-adherent wound dressing is readily extensible in all directions, and wherein said non-adherent wound dressing can be stretched and applied to irregularly shaped parts of the body.

11. A method as claimed in claim 10, wherein the sheet of melt-blown non-woven material to which the silicone gel precursor composition is applied is a perforated sheet.

12. A method as claimed in claim 11 further comprising:
    applying high frequency mechanical vibrations to the sheet to form perforations.

13. A method as claimed in claim 12, wherein said applying high frequency mechanical vibrations is carried out by passing the sheet through a nip formed between a sonotrode and a roller from which extend a plurality of perforating projections.

14. A method as claimed in claim 10, wherein the silicone gel precursor composition comprises a vinyl-substituted silicone and a hydride-containing silicone.

15. A method as claimed in claim 10, wherein curing of the silicone gel precursor composition is brought about by heating.

16. A method as claimed in claim 10, wherein said applying the silicone gel precursor composition is carried out by a dipping process, in which the substrate is introduced into, or transported through, a bath containing the silicone gel precursor composition.

* * * * *